(12) United States Patent
Lenz et al.

(10) Patent No.: US 6,716,581 B2
(45) Date of Patent: Apr. 6, 2004

(54) MANGANESE SUPEROXIDE DISMUTASE GENE POLYMORPHISM FOR PREDICTING CANCER SUSCEPTIBILITY

(75) Inventors: Heinz-Josef Lenz, Altadena, CA (US); Jan Stoehlmacher, Pasadena, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 09/824,629

(22) Filed: Apr. 2, 2001

(65) Prior Publication Data

US 2002/0039733 A1 Apr. 4, 2002

Related U.S. Application Data

(60) Provisional application No. 60/193,964, filed on Mar. 31, 2000.

(51) Int. Cl.$^7$ .......................... C07H 21/02; C07H 21/04; C12Q 1/68; C12P 19/34

(52) U.S. Cl. .............................. 435/6; 435/7.1; 435/7.4; 435/91.2; 536/23.2; 536/23.5; 536/24.31; 536/24.33

(58) Field of Search ............................ 435/7.1, 7.4, 6, 435/91.2; 536/23.5, 24.31, 24.33

(56) References Cited

FOREIGN PATENT DOCUMENTS

EP          0 691 401 A1      1/1996    ............. C12N/9/02

OTHER PUBLICATIONS

St. Clair D.K. and Holland J.C. (1991): Complementary DNA encoding human colon cancer manganese superoxide dismutase and the expression of its gene in human cells. Cancer Res. 51, 939–943.

Janssen, A.M.L. et al.(1998): Superoxide dismutases in relation to the overall survival of colorectal cancer patients. Br. J. Cancer 78 (8): 1051–1057.

Amstad, P.A. et al. (1997): Manganese superoxide dismutase expression inhibits soft agar growth in JB6 clone41 mouse epidermal cells. Carcinogenesis 18: (3): 479–84.

Sun Y. et al. (1988): Superoxide dismutase activity during dimethylhydrazine colon carcinogenesis and the effects of cholic acid and indole. Free Rad. Res. Commun. 4(5): 299–309.

Church S.L. et al. (1993): Increased manganese superoxide dismutase expression suppresses the malignant phenotype of human melanoma cells. Proc. Natl. Acad. Sci. USA 90:3113–3117.

Iyer, L. and Ratain, M.J. Pharacogenetics and Cancer Chemotherapy. Eur. J. Cancer 34:1493–9 (1998).

PCT/US01/10873 International Search Report.

Ambrosone, Christine B., et al., "Manganese Superoxide Dismutase (MnSOD) Genetic Polymorphisms, Dietary Antioxidants, and Risk of Breast Cancer," Cancer Research, vol. 59, No. 3, Feb. 1, 1999, pp. 602–606, XP002200091, ISSN: 0008–5472.

Shimoda–Matsubayashi, Satoe, et al., "Structural Dimorphism in the Mitochondrial Targeting Sequence in the Human Manganese Superoxide Dismutase Gene: A Predictive Evidence for Conformational Change to Influence Mitochondrial Transport and a Study of Allelic Association in Parkinson's Disease," Biochemical and Biophysical Research Communications, vol. 226, No. 2, 1996, pp. 561–565, XP002200092, ISSN: 0006–291X.

St. Clair, D.K., et al., "Complementary DNA Encoding Human Colon Cancer Manganese Superoxide Dismutase and the Expression of Its Gene in Human Cells," Cancer Research, vol. 51, No. 3, 1991, pp. 939–943, XP008003479, ISSN: 008–5472.

Kuratko, Connye N., "Increasing Dietary Lipid and Iron Content Decreases Manganese Superoxide Dismutase Activity in Colonic Mucosa," Nutrition and Cancer, vol. 28, No. 1, 1997, pp. 36–40, XP008003481, ISSN: 0163–5581.

Liu, R., et al., "Transfection and Expression of MNSOD CDNA Decreases Tumor Malignancy of Human Oral Squamous Carcinoma SCC–25 Cells," Human Gene Therapy, XX, XX, vol. 8, Mar. 20, 1997, pp. 585–595, XP002919704, ISSN: 1043–0342.

Stoehlmacher, Jan, et al., "The —9A1a/—9Val Polymorphism in the Mitochondrial Targeting Sequence of the Manganese Superoxide Dismutase Gene (MnSOD) is Associated with Age Among Hispanics with Colorectal Carcinoma," Oncology Reports, vol. 9, No. 2, Mar. 2002, pp. 235–238, XP008003480, ISSN: 1021–335X.

Oliva, M. R. et al. (1997): Genetic Alterations and Oxidative Metabolism in Sporadic Colorectal Tumors From a Spanish Community. Molecular Carcinogenesis 18: 232–243.

Ambrosone, C. B. et al. (1999): Manganese Superoxide Dismutase (MnSOD Genetic Polymorphisms, Dietary Antioxidants, and Risk of Breast Cancer. Can. Res. 59, 602–606.

Xu, Y. et al. (1999): Mutations in the promotor reveal a cause for the reduced expression of the human manganese superoxide dismutase gene in cancer cells. Oncogene 18(1): 93–102.

(List continued on next page.)

Primary Examiner—Carla J. Myers
(74) Attorney, Agent, or Firm—Bingham McCutchen LLP; David W. Maher

(57) ABSTRACT

The invention provides a method for determining the colorectal cancer susceptibility of a patient comprising determining a patient's genotype at the manganese superoxide dismutase (MnSOD) gene locus, wherein a patient with one or two alleles encoding alanine at position –9 of the signal peptide has an increased risk of developing colorectal cancer. Also provided are nucleic acid probes and kits for determining a patient's colorectal cancer risk.

15 Claims, 2 Drawing Sheets

OTHER PUBLICATIONS

Shimoda–Matsubayashi, S. et al. (1996): Structural Dimorphism in the Mitochondrial Trageting Sequence in the Human Manganase Superoxide Dismutase Gene. A predictive Evidence for Conformational Change to Influence Mitochondrial Transport and a Study of Allelic Association in Parkinson's Disease. Biochem. Biophys. Res. Commun. 226: 561–565.

Rosenblum, K.S. et al. (1996): On signal sequence polymorphisms and diseases of distribution. Proc. Natl. Acad. Sci. USA. 93: 4471–4473.

London, S. J. et al. (1999): Myeloperoxidase Genetic Polymorphism and Lung Cancer Risk. Can. Res. 57:5001–5003.

Janssen, A.M.L. et al. (1999): Superoxide dismutase in human colorectal cancer sequence. J Cancer Res. Clin. Oncol. 125: 327–335.

Van Driel, B. E. M. (1997): Expression of CuZn–and Mn–superoxide dismutase in human colorectal neoplasms. Free Rad. Biol. Med. 23: 435–444.

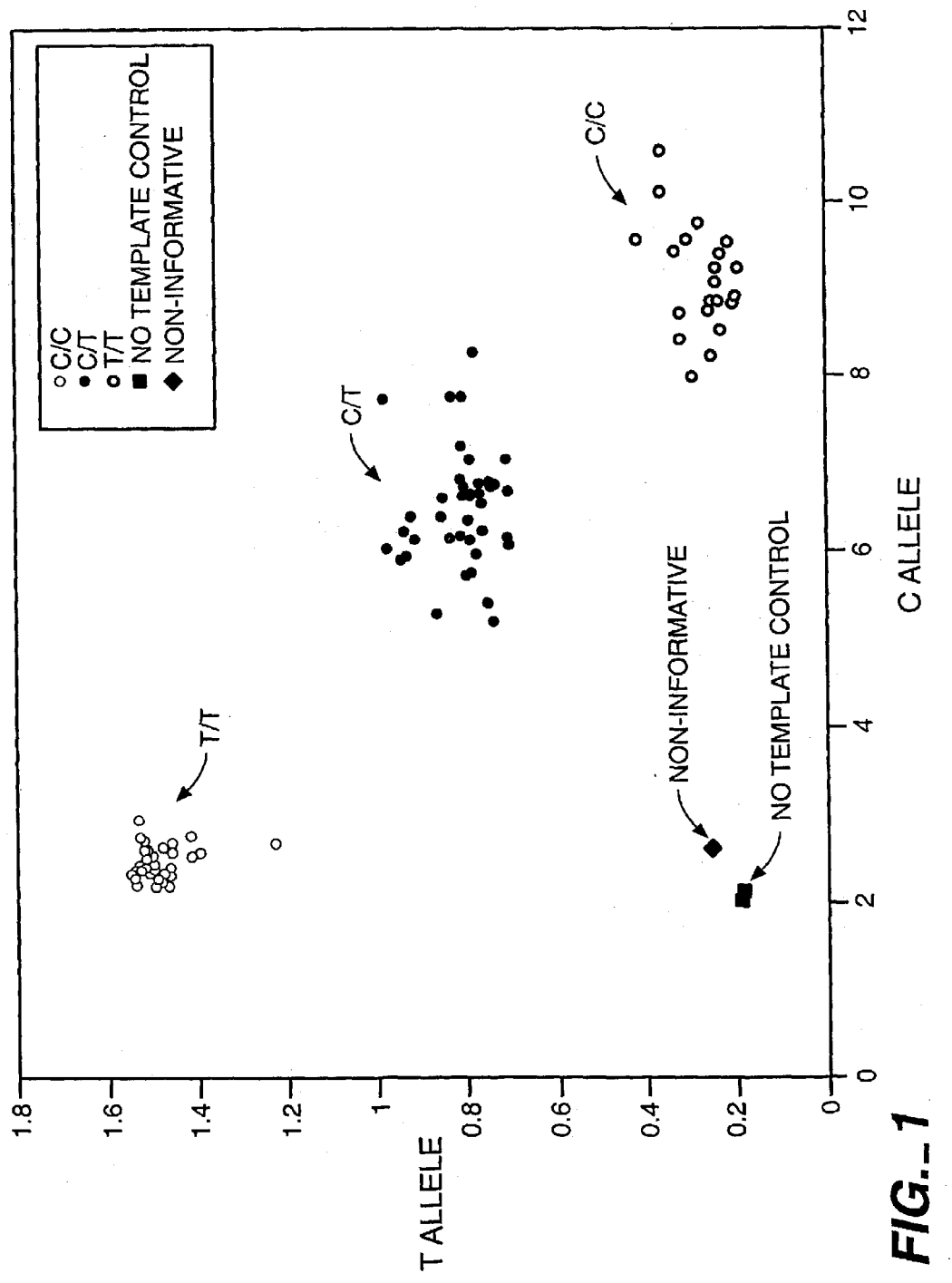
FIG._1

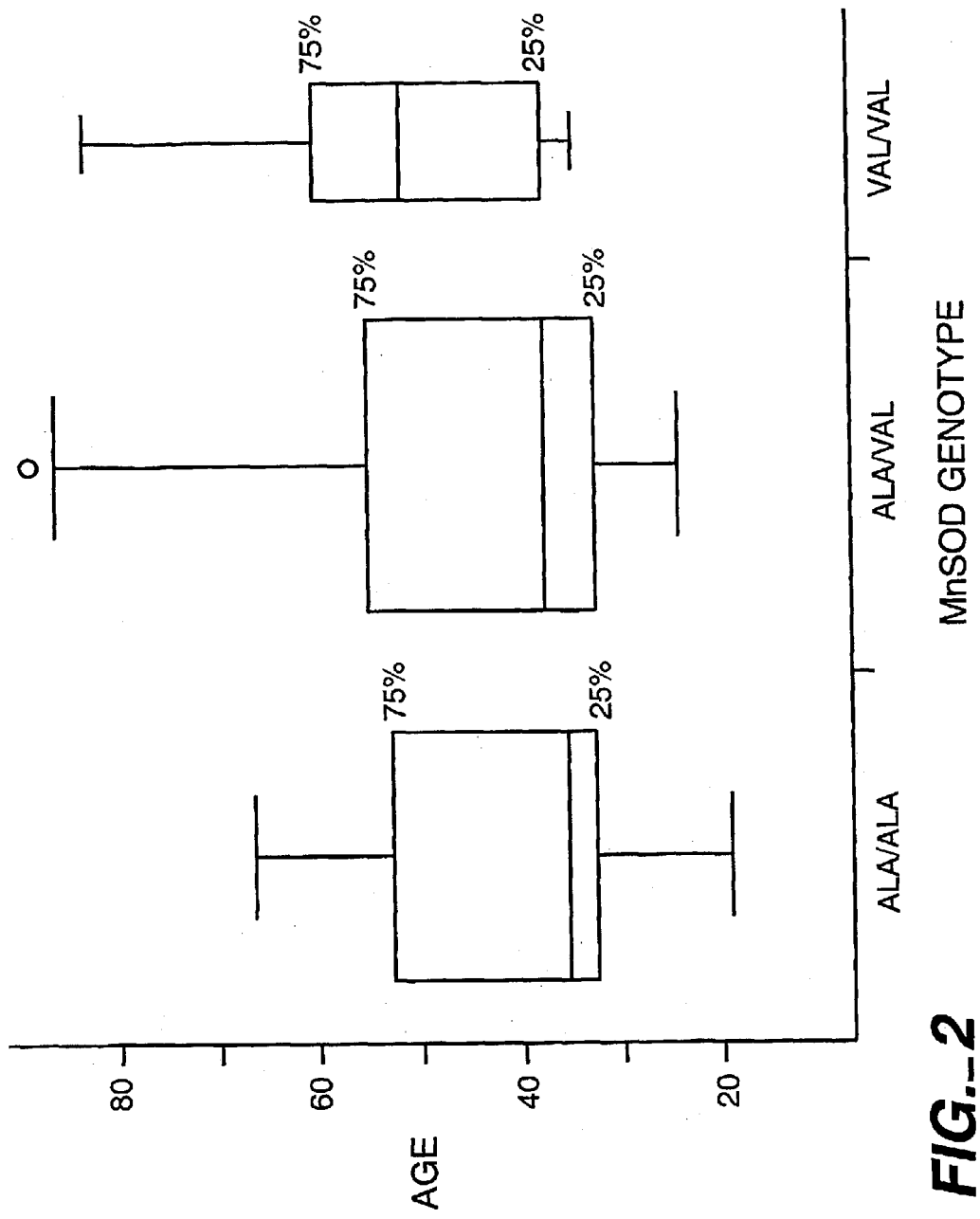
FIG._2

SEQUENCE LISTING

```
<160> NUMBER OF SEQ ID NOS: 6

<210> SEQ ID NO 1
<211> LENGTH: 418
<212> TYPE: DNA
<213> ORGANISM: Homo sapiens

<400> SEQUENCE: 1
cggtagcacc agcactagca gcatgttgag ccgggcagtg tgcgggtgag aagaaagggg      60
acccggtcac ggccccaagg gcgaaggggc tcgcggcggg cagggcctcc gcggcaatgg     120
cgacagtggc cgcaccgggc ctggcgggac cggggcacct gcaggcggtt ctcccgggag     180
tgcccggcgc ggcggctgga gcggggatcc gcagggaggg gacgcgggga ctcggggggac    240 gccgcgcgct gccgttcctc ggcagcccag cctgcgtaga cggtccccgc ggcgctgact     300
gaccgggctg tgctttctcg tcttcagcac cagcaggcag ctggctccgg ctttggggta     360
tctgggctcc aggcagaagc acagcctccc cgacctgccc tacgactacg gcgccctg      418

<210> SEQ ID NO 2
<211> LENGTH: 418
<212> TYPE: DNA
<213> ORGANISM: Homo sapiens

<400> SEQUENCE: 2
cggtagcacc agcactagca gcatgttgag ccgggcagtg tgcgggtgag aagaaagggg      60
acccggtcac ggccccaagg gcgaaggggc tcgcggcggg cagggcctcc gcggcaatgg     120
cgacagtggc cgcaccgggc ctggcgggac cggggcacct gcaggcggtt ctcccgggag     180
tgcccggcgc ggcggctgga gcggggatcc gcagggaggg gacgcgggga ctcggggggac    240 gccgcgcgct gccgttcctc ggcagcccag cctgcgtaga cggtccccgc ggcgctgact     300
gaccgggctg tgctttctcg tcttcagcac cagcaggcag ctggctccgg ttttggggta     360
```

```
tctgggctcc aggcagaagc acagcctccc cgacctgccc tacgactacg gcgccctg        418

<210> SEQ ID NO 3
<211> LENGTH: 21
<212> TYPE: DNA
<213> ORGANISM: Artificial Sequence
<220> FEATURE:
<223> OTHER INFORMATION: PCR primer

<400> SEQUENCE: 3
tgttttctcg tcttcagcac c                                                 21

<210> SEQ ID NO 4
<211> LENGTH: 18
<212> TYPE: DNA
<213> ORGANISM: Artificial Sequence
<220> FEATURE:
<223> OTHER INFORMATION: PCR primer

<400> SEQUENCE: 4
ggctgtgctt ctgcctgg                                                     18

<210> SEQ ID NO 5
<211> LENGTH: 21
<212> TYPE: DNA
<213> ORGANISM: Artificial Sequence
<220> FEATURE:
<223> OTHER INFORMATION: PCR primer

<400> SEQUENCE: 5
ataccccaaa gccggagcca g                                                 21

<210> SEQ ID NO 6
<211> LENGTH: 24
<212> TYPE: DNA
<213> ORGANISM: Artificial Sequence
<220> FEATURE:
<223> OTHER INFORMATION: PCR primer

<400> SEQUENCE: 6
agatacccca aaaccggagc cagc                                              24
```

MANGANESE SUPEROXIDE DISMUTASE GENE POLYMORPHISM FOR PREDICTING CANCER SUSCEPTIBILITY

RELATED APPLICATIONS

This invention claims priority to U.S. Provisional Application Ser. No. 60/193,964, filed Mar. 31, 2000.

FIELD OF THE INVENTION

This invention relates to the field of pharmacogenomics and specifically to the application of genetic polymorphism to diagnosing and treating diseases.

BACKGROUND OF THE INVENTION

In nature, organisms of the same species usually differ from each other in some aspects, e.g., their appearance. The differences are genetically determined and are referred to as polymorphism. At many gene loci, two or more alleles may occur (genetic polymorphism). Genetic polymorphism is defined as the occurrence in a population of two or more genetically determined alternative phenotypes due to different alleles. Polymorphism can be observed at the level of the whole individual (phenotype), in variant forms of proteins and blood group substances (biochemical polymorphism), morphological features of chromosomes (chromosomal polymorphism) or at the level of DNA in differences of nucleotides (DNA polymorphism).

Polymorphism may play a role in determining individual differences in the response to drugs. Cancer chemotherapy is limited by the predisposition of specific populations to drug toxicity or poor drug response (14). Thus, for example, pharmacogenetics (the effect of genetic differences on drug response) has been applied in cancer chemotherapy to understand the significant inter-individual variations in responses and toxicities to the administration of anti-cancer drugs, which may be due to genetic alterations in drug metabolizing enzymes or receptor expression. See co-pending U.S. application Ser. No. 09/715,764.

Polymorphism is also associated with cancer susceptibility (oncogenes, tumor suppressor genes and genes of enzymes involved in metabolic pathways) of individuals. In patients younger than 35 years, several markers of increased cancer risk have been identified. For example, prostate specific antigen (PSA) can be used for the early detection of prostate cancer in asymptomatic younger males, while particular cytochrome P4501A1 and gluthathione S-transferase M1 genotypes influence the risk of developing prostate cancer in younger patients. Similarly, mutations in the tumor suppressor gene, P53, are associated with brain tumors in young adults.

However, heretofore, polymorphism has not been associated with diagnosis and treatment of colorectal cancer. Presently, the assessment of the risk of developing colorectal cancer and diagnosis of colorectal cancer are carried out using screening methods in correlation with family history/relatives, proliferation assay and endoscopic screening. Advances in early diagnosis, screening procedures of high-risk individuals, the surgical approach and adjuvant therapy have not significantly impacted the prognosis of colorectal cancer in the last few decades. Thus, there exists a present need to develop more efficient methods and procedures for early diagnosis and treatment of colorectal cancer.

SUMMARY OF THE INVENTION

The invention provides a method for determining the colorectal cancer susceptibility of a patient comprising determining a patient's genotype at the manganese superoxide dismutase (MnSOD) gene locus, wherein a patient with one or two alleles encoding alanine at position −9 of the MnSOD signal peptide has an increased risk of developing colorectal cancer. Also provided are nucleic acid probes and kits for determining a patient's colorectal cancer risk.

In one embodiment, the invention comprises the use of the allelic variant of the polymorphic region of the MnSOD gene. These methods of use include prognostic, diagnostic, and therapeutic methods. For example, the methods include using nucleic acids encompassing the polymorphic region as probes or primers to determine whether a subject has or is at risk of developing colorectal cancer. Accordingly, the invention provides methods for predicting or diagnosing colorectal cancer associated with an aberrant MnSOD gene activity.

In another embodiment, the invention provides a kit for amplifying and/or for determining the molecular structure of at least a portion of the MnSOD gene, comprising a probe or primer capable of hybridizing to the MnSOD gene and instructions for use. In one embodiment, the probe or primer is capable of hybridizing to an allelic variant of the MnSOD gene. In a preferred embodiment, the polymorphic region is located at position 351 of SEQ ID NO: 1. In a preferred embodiment, the invention provides a kit for determining whether a subject has or is at risk of developing colorectal cancer.

Other features and advantages of the invention will be apparent from the following detailed description and claims.

BRIEF DESCRIPTION OF THE DRAWINGS

FIG. 1 is a plot of MnSOD alleles plotted as a function of Relative Fluorogenic Units.

FIG. 2 shows the association between MnSOD genotype and age among Hispanics with colorectal cancer.

DETAILED DESCRIPTION OF THE PREFERRED EMBODIMENTS

It has been shown that enzymes involved in oxidative metabolism play an important role in the carcinogenesis process because oxidative stress, caused by decreased levels of free radical scavengers such as superoxide dismutase (SOD), leads to DNA strand breaks, mitochondria and protein damage (1, 11, 12). It has further been shown that increased SOD levels suppress tumorigenicity in human melanoma cells (13). Oxidative stress, resulting from the imbalance between pro- and antioxidant states, causes damage of DNA, mitochondria, proteins and cell membranes. MnSOD and myeloperoxidase (MPO), two enzymes that may influence the pool of free radicals in the cell, have been demonstrated to determine the risk of breast and lung cancer (2, 6). However, no predictive molecular marker for colon cancer risk has been established to date to identify individuals with high risk to develop cancer at a young age. This invention is based on the recognition that polymorphisms of the genes that influence the balance between prooxidant and antioxidant states of the cell will predict cancer risk in association with the individual's age. Thus, the polymorphism of the manganese superoxide dismutase (MnSOD) gene may be used to identify young individuals with high risk for cancer and select them for further diagnostic procedures to maximize the benefits of treatment by detecting the cancer in early stages of the disease.

Three distinct SODs are known in human cells: the mitochondrial MnSOD, the extracellular copper zinc (CuZnSOD) and the cytosolic copper zinc superoxide dismutase (CuZnSOD). The main function of the SOD enzymes is to reduce the free radicals in the cell by detoxification of superoxide anions to hydrogen peroxide and oxygen, thereby reducing the hazard of oxidative stress in the cell. Recently, it has been shown that a T to C substitution in the mitochondrial targeting sequence of the MnSOD gene leads to an amino acid codon change at −9 position in the signal peptide from valine (GTT) to alanine (GCT). Further it has been found that this amino acid substitution changes the secondary structure of the protein from a α-helical structure to a β-pleated sheet conformation (4). Rosenblum et al. suggest that this structural change could lead to a decreased defense capacity of the mitochondria and so alter the integrity of the cell (5).

The present invention is based at least in part on the discovery of a correlation between the existence of the polymorphic region within the human MnSOD gene and a carcinogenic condition, specifically colorectal cancer. The human MnSOD gene contains a polymorphic region within its mitochondrial targeting sequence (MTS) for encoding the signal peptide. A T to C substitution in the mitochondrial targeting sequence of the MnSOD gene leads to an amino acid codon change at −9 position in the signal peptide from valine (GTT) to alanine (GCT). Signal peptides with a valine at the −9 position are referred to herein as valine signal peptides and signal peptides with an alanine at the −9 position are referred to herein as the alanine signal peptides.

This polymorphism of the MnSOD gene is biallelic. Thus, individuals maybe homozygous for the alanine (Ala) signal peptide, homozygous for the valine (Val) signal peptide or heterozygous. These genotypes are characterized herein as follows:

Homozygous for Ala: Ala/Ala or C/C

Homozygous for Val: Val/Val or T/T

Heterozygous: Ala/Val or C/T

The invention is based on the discovery that Ala/Ala individuals are likely to develop colorectal cancer at a younger age compared to Ala/Val individuals who, in turn, are likely to develop colorectal cancer at a younger age compared to Val/Val individuals. Thus, a T to C substitution at position 351 of the mitochondrial targeting sequence portion of the MnSOD gene shown in Table 3 increases the likelihood of an individual developing colorectal cancer at a young age.

Accordingly, the invention provides methods and kits to determine whether a subject has or is at risk of developing colorectal cancer by determining the subject's genotype at the MnSOD genetic locus. Other aspects of the invention are described below or will be apparent to one of skill in the art in light of the present disclosure.

For convenience, the meaning of certain terms and phrases employed in the specification, examples, and appended claims are provided below.

DEFINITIONS

The term "allele", which is used interchangeably herein with "allelic variant" refers to alternative forms of a gene or portions thereof. Alleles occupy the same locus or position on homologous chromosomes. When a subject has two identical alleles of a gene, the subject is said to be homozygous for the gene or allele. When a subject has two different alleles of a gene, the subject is said to be heterozygous for the gene. Alleles of a specific gene can differ from each other in a single nucleotide, or several nucleotides, and can include substitutions, deletions, and insertions of nucleotides. An allele of a gene can also be a form of a gene containing a mutation.

The term "allelic variant of a polymorphic region of the MnSOD gene" refers to a region of the MnSOD gene having one of a plurality of nucleotide sequences found in that region of the gene in other individuals.

"Biological activity" or "bioactivity" or "activity" or "biological function", which are used interchangeably, for the purposes herein when applied to MnSOD means an effector or antigenic function that is directly or indirectly performed by the MnSOD polypeptide (whether in its native or denatured conformation), or by any subsequence (fragment) thereof.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

The expression "amplification of polynucleotides" includes methods such as PCR, ligation amplification (or ligase chain reaction, LCR) and amplification methods based on the use of Q-beta replicase. These methods are well known and widely practiced in the art. See, e.g., U.S. Pat. Nos. 4,683,195 and 4,683,202 and Innis et al., 1990 (for PCR); and Wu, D. Y. et al. (1989) *Genomics* 4:560–569 (for LCR). In general, the PCR procedure describes a method of gene amplification which is comprised of (i) sequence-specific hybridization of primers to specific genes within a DNA sample (or library), (ii) subsequent amplification involving multiple rounds of annealing, elongation, and denaturation using a DNA polymerase, and (iii) screening the PCR products for a band of the correct size. The primers used are oligonucleotides of sufficient length and appropriate sequence to provide initiation of polymerization, i.e. each primer is specifically designed to be complementary to each strand of the genomic locus to be amplified.

Reagents and hardware for conducting PCR are commercially available. Primers useful to amplify sequences from a particular gene region are preferably complementary to, and hybridize specifically to sequences in the target region or in its flanking regions. Nucleic acid sequences generated by amplification may be sequenced directly. Alternatively the amplified sequence(s) may be cloned prior to sequence analysis. A method for the direct cloning and sequence analysis of enzymatically amplified genomic segments has been described by Scharf, 1986.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

The term "genotype" refers to the specific allelic composition of an entire cell or a certain gene, whereas the term "phenotype' refers to the detectable outward manifestations of a specific genotype.

As used herein, the term "gene" or "recombinant gene" refers to a nucleic acid molecule comprising an open reading frame and including at least one exon and (optionally) an intron sequence. The term "intron" refers to a DNA sequence present in a given gene which is spliced out during mRNA maturation.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, though preferably less than 25% identity, with one of the sequences of the present invention.

The term "a homolog of a nucleic acid" refers to a nucleic acid having a nucleotide sequence having a certain degree of homology with the nucleotide sequence of the nucleic acid or complement thereof. A homolog of a double stranded nucleic acid having SEQ ID NO: x is intended to include nucleic acids having a nucleotide sequence which has a certain degree of homology with SEQ ID NO: x or with the complement thereof. Preferred homologs of nucleic acids are capable of hybridizing to the nucleic acid or complement thereof.

The term "interact" as used herein is meant to include detectable interactions between molecules, such as can be detected using, for example, a hybridization assay. The term interact is also meant to include "binding" interactions between molecules. Interactions may be, for example, protein-protein, protein-nucleic acid, protein-small molecule or small molecule-nucleic acid in nature.

The term "isolated" as used herein with respect to nucleic acids, such as DNA or RNA, refers to molecules separated from other DNAs or RNAs, respectively, that are present in the natural source of the macromolecule. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides.

The term "mismatches" refers to hybridized nucleic acid duplexes which are not 100% homologous. The lack of total homology may be due to deletions, insertions, inversions, substitutions or frameshift mutations.

As used herein, the term "nucleic acid" refers to polynucleotides such as deoxyribonucleic acid (DNA), and, where appropriate, ribonucleic acid (RNA). The term should also be understood to include, as equivalents, derivatives, variants and analogs of either RNA or DNA made from nucleotide analogs, and, as applicable to the embodiment being described, single (sense or antisense) and double-stranded polynucleotides. Deoxyribonucleotides include deoxyadenosine, deoxycytidine, deoxyguanosine, and deoxythymidine. For purposes of clarity, when referring herein to a nucleotide of a nucleic acid, which can be DNA or an RNA, the terms "adenosine", "cytidine", "guanosine", and thymidine" are used. It is understood that if the nucleic acid is RNA, a nucleotide having a uracil base is uridine.

The terms "oligonucleotide" or "polynucleotide", or "portion," or "segment" thereof refer to a stretch of polynucleotide residues which is long enough to use in PCR or various hybridization procedures to identify or amplify identical or related parts of mRNA or DNA molecules. The polynucleotide compositions of this invention include RNA, cDNA, genomic DNA, synthetic forms, and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoamidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

The term "nucleotide sequence complementary to the nucleotide sequence set forth in SEQ ID NO: x" refers to the nucleotide sequence of the complementary strand of a nucleic acid strand having SEQ ID NO: x. The term "complementary strand" is used herein interchangeably with the term "complement". The complement of a nucleic acid strand can be the complement of a coding strand or the complement of a non-coding strand. When referring to double stranded nucleic acids, the complement of a nucleic acid having SEQ ID NO: x refers to the complementary strand of the strand having SEQ ID NO: x or to any nucleic acid having the nucleotide sequence of the complementary strand of SEQ ID NO: x. When referring to a single stranded nucleic acid having the nucleotide sequence SEQ ID NO: x, the complement of this nucleic acid is a nucleic acid having a nucleotide sequence which is complementary to that of SEQ ID NO: x. The nucleotide sequences and complementary sequences thereof are always given in the 5' to 3' direction. The term "complement" and "reverse complement" are used interchangeably herein.

A "non-human animal" of the invention can include mammals such as rodents, non-human primates, sheep, goats, horses, dogs, cows, chickens, amphibians, reptiles, etc. Preferred non-human animals are selected from the rodent family including rat and mouse, most preferably mouse, though transgenic amphibians, such as members of the Xenopus genus, and transgenic chickens can also provide important tools for understanding and identifying agents which can affect, for example, embryogenesis and tissue formation. The term "chimeric animal" is used herein to refer to animals in which an exogenous sequence is found, or in which an exogenous sequence is expressed in some but not all cells of the animal. The term "tissue-specific chimeric animal" indicates that an exogenous sequence is present and/or expressed or disrupted in some tissues, but not others.

The term "polymorphism" refers to the coexistence of more than one form of a gene or portion thereof. A portion of a gene of which there are at least two different forms, i.e., two different nucleotide sequences, is referred to as a "polymorphic region of a gene". A polymorphic region can be a single nucleotide, the identity of which differs in different alleles.

A "polymorphic gene" refers to a gene having at least one polymorphic region.

The invention described herein relates to methods and compositions for determining the allele present at the MnSOD gene locus. Probes can be used to directly determine the genotype of the sample or can be used simultaneously with or subsequent to amplification. The term "probes" includes naturally occurring or recombinant single- or double-stranded nucleic acids or chemically synthesized nucleic acids. They may be labeled by nick translation, Klenow fill-in reaction, PCR or other methods well known in the art. Probes of the present invention, their preparation and/or labeling are described in Sambrook, J. et al. (1989) Molecular Cloning: A Laboratory Manual, Cold Spring Harbor Laboratory, NY; or Ausubel, F. M. et al. (1995) Current Protocols in Molecular Biology, John Wiley & Sons, New York NY, both incorporated herein by reference. A probe can be a polynucleotide of any length suitable for selective hybridization to a nucleic acid containing a polymorphic region of the invention. Length of the probe used will depend, in part, on the nature of the assay used and the hybridization conditions employed.

In one embodiment of the invention, probes are labeled with two fluorescent dye molecules to form so-called "molecular beacons" (Tyagi, S. and Kramer, F. R. (1996) Nat. Biotechnol. 14:303-8). Such molecular beacons signal binding to a complementary nucleic acid sequence through relief of intramolecular fluorescence quenching between dyes bound to opposing ends on an oligonucleotide probe. The use of molecular beacons for genotyping has been described (Kostrikis L. G. (1998) Science 279:1228-9) as has the use of multiple beacons simultaneously (Marras, S. A. (1999) Genet. Anal. 14:151-6). A quenching molecule is useful with a particular fluorophore if it has sufficient sp[ectral overlap to substantially inhibit fluorescence of the fluorophore when the two are held proixmal to one another, such as in a molecular beacon, or when attached to the ends of an oligonucleotide probe from about 1 to about 25 nucleotides.

Labeled probes also can be used in conjunction with amplification of a polymorphism. Holland et al. (Holland et al. (1991) Proc. Natl. Acad. Sci., 88:7276–7280), U.S. Pat. No. 5,210,015 to Gelfand et al. describe fluorescence-based approaches to provide real time measurements of amplification products during PCR. Such approaches have either employed intercalating dyes (such as ethidium bromide) to indicate the amount of double-stranded DNA present, or they have employed probes containing fluorescence-quencher pairs (also referred to as the "Taq-Man" approach) where the probe is cleaved during amplification to release a fluorescent molecule whose concentration is proportional to the amount of double-stranded DNA present. During amplification, the probe is digested by the nuclease activity of a polymerase when hybridized to the target sequence to cause the fluorescent molecule to be separated from the quencher molecule, thereby causing fluorescence from the reporter molecule to appear. The Taq-Man approach uses a probe containing a reporter molecule—quencher molecule pair that specifically anneals to a region of a target polynucleotide containing the poymorphism.

Probes can be affixed to surfaces for use as "gene chips." Such gene chips can be used to detect genetic variations by a number of techniques known to one of skill in the art. In one technique, oligonucleotides are arrayed on a gene chip for determining the DNA sequence of a by the sequencing by hybridization approach, such as that outlined in U.S. Pat. Nos. 6,025,136 and 6,018,041. The probes of the invention also can be used for fluorescent detection of a genetic sequence. Such techniques have been described, for example, in U.S. Pat. Nos. 5,968,740 and 5,858,659. A probe also can be affixed to an electrode surface for the electrochemical detection of nucleic acid sequences such as described by Kayyem et al. U.S. Pat. No. 5,952,172 and by Kelley, S. O. et al. (1999)Nucleic Acids Res. 27:4830-7.

The terms "protein", "polypeptide" and "peptide" are used interchangeably herein when referring to a gene product.

The term "recombinant protein" refers to a polypeptide which is produced by recombinant DNA techniques, wherein generally, DNA encoding the polypeptide is inserted into a suitable expression vector which is in turn used to transform a host cell to produce the heterologous protein.

The term "treating" as used herein is intended to encompass curing as well as ameliorating at least one symptom of the condition or disease.

As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

The term "wild-type allele" refers to an allele of a gene which, when present in two copies in a subject results in a wild-type phenotype. There can be several different wild-type alleles of a specific gene, since certain nucleotide changes in a gene may not affect the phenotype of a subject having two copies of the gene with the nucleotide changes.

NUCLEIC ACIDS

Table 3 lists a partial sequence of the MnSOD gene, showing the point mutation of the subject polymorphism. As can be seen in Table 3, the polymorphism is a change from a T to a C at position 351 of SEQ ID NO: 1, which results in a change from a valine to an alanine at amino acid residue −9 of the encoded protein. The nucleotide sequence of this allele is set forth in SEQ ID NO: 2 (which is identical to SEQ ID NO: 1, except for nucleotide 351, which is a C).

The nucleic acid sequences, SEQ ID NO: 1 and 2 can be the basis for probes or primers, e.g., in methods for determining the identity of the allelic variant of the MnSOD polymorphic region. Thus, they can be used in the methods of the invention to determine whether a subject is at risk of developing colorectal cancer. They can also be used to prepare MnSOD polypeptides, which can be used in gene therapy or for preparing reagents, e.g., antibodies, for detecting the MnSOD signal peptide or its allelic variant.

Preferably the methods of the invention use nucleic acids from vertebrate genes encoding MnSOD. Particularly preferred vertebrate nucleic acids are mammalian nucleic acids. A particularly preferred nucleic acid used in the methods of the invention is a human nucleic acid, such as a nucleic acid comprising the sequences set forth in any of SEQ ID NOS. 1–2 or complements thereof.

Primers for use in the methods of the invention are nucleic acids which hybridize to a nucleic acid sequence which is adjacent to the region of interest (nucleotide 351 of SEQ ID NO: 1) or which covers the region of interest and is extended. A primer can be used alone in a detection method, or a primer can be used together with at least one other primer or probe in a detection method. Primers can also be used to amplify at least a portion of a nucleic acid. Probes for use in the methods of the invention are nucleic acids which hybridize to the region of interest and which are not further extended. For example, a probe is a nucleic acid which hybridizes to the polymorphic region of the MnSOD gene, and which by hybridization or absence of hybridization to the DNA of a subject will be indicative of the identity of the allelic variant of the polymorphic region of the MnSOD gene.

Preferred primers comprise a nucleotide sequence which comprises a region having a nucleotide sequence which hybridizes under stringent conditions to about 6, 8, 10, or 12, preferably 25, 30, 40, 50, or 75 consecutive nucleotides of the MnSOD gene. In an even more preferred embodiment, the primer has a nucleotide sequence set forth in any of SEQ ID Nos. 3–6, complements thereof, allelic variants thereof, or complements of allelic variants thereof.

Primers can be complementary to nucleotide sequences located close to each other or further apart, depending on the use of the amplified DNA. For example, primers can be chosen such that they amplify DNA fragments of at least about 10 nucleotides or as much as several kilobases. Preferably, the primers of the invention will hybridize selectively to nucleotide sequences located about 150 to about 350 nucleotides apart.

For amplifying at least a portion of a nucleic acid, a forward primer (i.e., 5' primer) and a reverse primer (i.e., 3' primer) will preferably be used. Forward and reverse primers hybridize to complementary strands of a double stranded nucleic acid, such that upon extension from each primer, a double stranded nucleic acid is amplified.

Yet other preferred primers of the invention are nucleic acids which are capable of selectively hybridizing to an allelic variant of a polymorphic region of the MnSOD gene. Thus, such primers can be specific for the MnSOD gene sequence, so long as they have a nucleotide sequence which is capable of hybridizing to the MnSOD gene. Preferred primers are capable of specifically hybridizing to an allelic variant in which nucleotide 351 of SEQ ID NO: 1 is a C.

The nucleic acids set forth in SEQ ID NO: 1 and 2, and portions thereof can also be used as probes in the methods of the invention. Preferred probes of the invention are capable of hybridizing specifically to a region overlapping nucleotide 351 of SEQ ID NO: 1. In one embodiment, the probe overlapping nucleotide 351 of SEQ ID NO: 1 is capable of hybridizing specifically to a nucleotide sequence wherein nucleotide 351 is a C.

The probe or primer may further comprises a label attached thereto, which, e.g., is capable of being detected, e.g. the label group is selected from amongst radioisotopes, fluorescent compounds, enzymes, and enzyme co-factors.

Additionally, the isolated nucleic acids used as probes or primers may be modified to become more stable. Exemplary nucleic acid molecules which are modified include phosphoramidate, phosphothioate and methylphosphonate analogs of DNA (see also U.S. Pat. Nos. 5,176,996; 5,264,564; and 5,256,775).

The nucleic acids used in the methods of the invention can also be modified at the base moiety, sugar moiety, or phosphate backbone, for example, to improve stability of the molecule. The nucleic acids, e.g., probes or primers, may include other appended groups such as peptides (e.g., for targeting host cell receptors in vivo), or agents facilitating transport across the cell membrane (see, e.g., Letsinger et al., 1989, Proc. Natl. Acad. Sci. U.S.A. 86:6553–6556; Lemaitre et al., 1987, Proc. Natl. Acad. Sci. 84:648–652; PCT Publication No. WO 88/09810, published Dec. 15, 1988), hybridization-triggered cleavage agents. (See, e.g., Krol et al., 1988, BioTechniques 6:958–976) or intercalating agents. (See, e.g., Zon, 1988, Pharm. Res. 5:539–549). To this end, the nucleic acid used in the methods of the invention may be conjugated to another molecule, e.g., a peptide, hybridization triggered cross-linking agent, transport agent, hybridization-triggered cleavage agent, etc.

The isolated nucleic acids used in the methods of the invention may also comprise at least one modified sugar moiety selected from the group including but not limited to arabinose, 2-fluoroarabinose, xylulose, and hexose or, alternatively, comprise at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

The nucleic acids, or fragments thereof, to be used in the methods of the invention can be prepared according to methods well known in the art and described, e.g., in Sambrook, J. Fritsch, E. F., and Maniatis, T. (1989) Molecular Cloning: A Laboratory Manual, Cold Spring Harbor Laboratory Press, Cold Spring Harbor, N.Y. For example, discrete fragments of the DNA can be prepared and cloned using restriction enzymes. Alternatively, discrete fragments can be prepared using the Polymerase Chain Reaction (PCR) using primers having an appropriate sequence.

Oligonucleotides may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448–7451), etc.

POLYPEPTIDES

The present invention provides for methods that use polypeptides such as the isolated signal peptide of MnSOD or its allelic variants, or MnSOD or the allelic variants of MnSOD (henceforth, subject polypeptides or subject proteins). Such polypeptides are isolated from, or otherwise substantially free of other cellular proteins. The term "substantially free of other cellular proteins" (also referred to herein as "contaminating proteins") or "substantially pure or purified preparations" are defined as encompassing preparations of polypeptides having less than about 20% (by dry weight) contaminating protein, and preferably having less than about 5% contaminating protein. Functional forms of the subject polypeptides can be prepared, for the first time, as purified preparations by using a cloned gene as described herein.

The methods of the invention may also use polypeptides which have an amino acid sequence which is at least about 60%, 70%, 80%, 85%, 90%, or 95% and, more preferably, about 97, 98, or 99% identical or homologous to the signal peptide of MnSOD or its allelic variants, or MnSOD or the allelic variants of MnSOD. The polypeptides can be recombinant proteins, and can be, e.g., produced in vitro from nucleic acids comprising a specific allele of the MnSOD polymorphic region. For example, recombinant polypeptide preferred by the present invention can be encoded by a nucleic acid, which is at least 85% homologous and more preferably 90% homologous and most preferably 95–99% homologous with a nucleotide sequence set forth in SEQ ID NOS. 1 or 2, and comprises an allele of a polymorphic region that differs from that set forth in SEQ ID Nos. 1 and 2. In a preferred embodiment, the polypeptides are mammlian proteins and more preferably human proteins, such as MnSOD or the signal peptide of MnSOD, or allelic variants thereof. Full length proteins or fragments corresponding to one or more particular motifs and/or domains or to arbitrary sizes, for example, at least 5, 10, 25, 50, 75 and 100, amino acids in length are within the scope of the present invention.

In general, polypeptides referred to herein as having an activity (e.g., are "bioactive") of the MnSOD or its signal peptide or their allelic variants are defined as polypeptides which mimic or antagonize all or a portion of the biological/biochemical activities of MnSOD or its signal peptide or their allelic variants. Other biological activities of the subject proteins are described herein or will be reasonably apparent to those skilled in the art. According to the present invention, a polypeptide has biological activity if it is a specific agonist or antagonist of MnSOD or its signal peptide or their allelic variants. Assays for determining biological activities of polypeptides are well known in the art.

Moreover, it will be generally appreciated that, under certain circumstances, it may be advantageous to provide homologs of one of the subject polypeptides which function in a limited capacity as either agonists (mimetic) or antagonists of the subject polypeptides, in order to promote or inhibit only a subset of the biological activities of the naturally-occurring form of the protein. Thus, specific biological effects can be elicited by treatment with a homolog of limited function, and with fewer side effects relative to treatment with agonists or antagonists which are directed to all of the biological activities of naturally occurring forms of the subject proteins.

Homologs of each of the subject proteins can be generated by mutagenesis, such as by discrete point mutation(s), or by truncation. For instance, mutation can give rise to homologs which retain substantially the same, or merely a subset, of the biological activity of the subject polypeptide from which it was derived. Alternatively, antagonistic forms of the protein can be generated which are able to inhibit the function of the naturally occurring form of the protein, such as by competitively binding to the receptor of the subject protein.

Also included are recombinant homologs of the subject polypeptides which are resistant to proteolytic cleavage, as for example, due to mutations which alter ubiquitination or other enzymatic targeting associated with the protein.

The subject polypeptides may also be chemically modified to create derivatives by forming covalent or aggregate conjugates with other chemical moieties, such as glycosyl groups, lipids, phosphate, acetyl groups and the like. Covalent derivatives of the subject proteins can be prepared by linking the chemical moieties to functional groups on amino acid sidechains of the protein or at the N-terminus or at the C-terminus of the polypeptide.

Modification of the structure of the subject the subject polypeptides can be for such purposes as enhancing therapeutic or prophylactic efficacy, stability (e.g., ex vivo shelf life and resistance to proteolytic degradation), or post-translational modifications (e.g., to alter phosphorylation pattern of protein). Such modified peptides, when designed to retain at least one activity of the naturally-occurring form of the protein, or to produce specific antagonists thereof, are considered functional equivalents of the subject polypeptides described in more detail herein. Such modified peptides can be produced, for instance, by amino acid substitution, deletion, or addition. The substitutional variant may be a substituted conserved amino acid or a substituted non-conserved amino acid.

For example, it is reasonable to expect that an isolated replacement of a leucine with an isoleucine or valine, an aspartate with a glutamate, a threonine with a serine, or a similar replacement of an amino acid with a structurally related amino acid (i.e. isosteric and/or isoelectric mutations) will not have a major effect on the biological activity of the resulting molecule. Conservative replacements are those that take place within a family of amino acids that are related in their side chains. Genetically encoded amino acids can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine. (see, for example, Biochemistry, 2.sup.nd ed., Ed. by L. Stryer, W H Freeman and Co.: 1981). Whether a change in the amino acid sequence of a peptide results in a functional homolog of the subject protein (e.g., functional in the sense that the resulting polypeptide mimics or antagonizes the wild-type form) can be readily determined by assessing the ability of the variant peptide to produce a response in cells in a fashion similar to the wild-type protein, or competitively inhibit such a response. Polypeptides in which more than one replacement has taken place can readily be tested in the same manner.

PREDICTIVE MEDICINE AND PHARMACOGENOMICS

The invention further features predictive medicines, which are based, at least in part, on determination of the identity of the MnSOD polymorphic region which is associated with colorectal cancer.

For example, information obtained using the diagnostic assays described herein (alone or in conjunction with information on another genetic defect, which contributes to the same disease) is useful for diagnosing or confirming that a symptomatic subject has an allele of a polymorphic region which is associated with colorectal cancer. Alternatively, the information (alone or in conjunction with information on another genetic defect, which contributes to the same disease) can be used prognostically for predicting whether a non-symptomatic subject is likely to develop colorectal cancer. Based on the prognostic information, a doctor can recommend a regimen (e.g. diet or exercise) or therapeutic protocol, useful for preventing or delaying onset of colorectal cancer in the individual.

In addition, knowledge of the identity of a particular MnSOD allele in an individual (the MnSOD genetic profile), alone or in conjunction with information on other genetic defects contributing to the same disease (the genetic profile of the particular disease) allows customization of therapy for a particular disease to the individual's genetic profile, the goal of "pharmacogenomics". For example, an individual's MnSOD genetic profile can enable a doctor: 1) to more effectively prescribe a drug that will address the molecular basis of the disease or condition; and 2) to better determine the appropriate dosage of a particular drug. For example, the expression level of the MnSOD gene, alone or in conjunction with the expression level of other genes, known to contribute to the same disease, can be measured in many patients at various stages of the disease to generate a transcriptional or expression profile of the disease. Expression patterns of individual patients can then be compared to the expression profile of the disease to determine the appropriate drug and dose to administer to the patient.

The ability to target populations expected to show the highest clinical benefit, based on the MnSOD or disease genetic profile, can enable: 1) the repositioning of marketed drugs with disappointing market results; 2) the rescue of drug candidates whose clinical development has been discontinued as a result of safety or efficacy limitations, which are patient subgroup-specific; and 3) an accelerated and less costly development for drug candidates and more optimal drug labeling (e.g. since the use of MnSOD as a marker is useful for optimizing effective dose).

Prognostic and Diagnostic Assays

The present methods provide means for determining if a subject has (diagnostic) or is at risk of developing (prognostic) colorectal cancer. In one embodiment, the invention provides a method for determining the cancer susceptibility of a patient by determining the patient's genotype at the genetic locus MnSOD and classifying the patient's colorectal cancer susceptibility wherein the presence of the MnSOD allele encoding alanine indicates high risk.

As described herein, genotypes can be determined from nucleic acids, RNA or DNA isolated from the patient with or without amplification of the genetic locus. A number of methods are suitable for determining the genotype.

Accordingly, the invention provides a method for determining whether a subject has, or is at a risk of developing, colorectal cancer comprising determining the identity of the allelic variant of the MnSOD gene in a nucleic acid obtained from the subject. Briefly, this method comprises (i) amplifying a first DNA fragment comprising the polymorphic region of the MnSOD genetic locus; (ii) determining the genotype of the patient at the MnSOD locus. In preferred embodiments, the methods of the invention can be characterized as comprising detecting, in a sample of cells from the subject, the presence or absence of a specific allelic variant of a polymorphic region of the MnSOD gene. In a preferred embodiment, the allelic differences is a difference in the identity of nucleotide 351 in SEQ ID NO: 1.

In one embodiment, the method comprises contacting the subject's sample nucleic acid comprising the MnSOD gene with a probe or primer which hybridizes to the polymorphic region of the mitochondrial targeting sequence of the MnSOD gene, which includes nucleotide 351 of SEQ ID NO:1. In various embodiments, the probe or primer has a nucleotide sequence from about 15 to about 30 nucleotides, and/or is detectably labeled.

In essence, determining the identity of the allelic variant comprises determining the identity of at least one nucleotide of the polymorphic region of the mitochondrial targeting sequence of the MnSOD gene. As discussed more fully below, many methods are available to determine the identity of an allelic variant of a gene, including, but not limited to, methods that comprise performing a restriction enzyme site analysis, methods that are carried out by single-stranded conformation polymorphism, by allele specific hybridization, by an oligonucleotide ligation assay. Most preferably, the methods are applied to a human subject so that the MnSOD gene being analyzed is a human MnSOD gene.

In a preferred embodiment, the invention provides a method for determining risk of colorectal cancer in a subject, comprising the steps of: (a) determining the base identity of a portion of genomic DNA from the subject's cell sample, said genomic DNA comprising an MnSOD gene comprising a mitochondrial targeting sequence, said portion corresponding to position 351 as defined in SEQ ID NO:1 of said MnSOD gene in said mitochondrial targeting sequence; and (b) correlating said base identity with a risk for colorectal cancer. In this method the base identity of position 351 may be determined by sequencing a portion of said mitochondrial targeting sequence of said MnSOD gene containing position 351. Alternatively, the base identity of position 351 is determined by digesting the portion of the mitochondrial targeting sequence of the MnSOD gene with a restriction endonuclease appropriate to determine the base identity of position 351. In another embodiment, the base identity is determined by examining an RNA fraction from said subject's cell sample, whereby the identity of said genomic DNA at said position 351 can be determined. In the above methods the subject's risk for developing colorectal cancer is assessed to be greater than that of the unaffected relevant population when the base identity at said position 351 is homozygous for C, i.e., the subject's genotype is Ala/Ala (or C/C), or heterozygous, i.e., Ala/Val (or C/T). Most preferably, the methods use the subject's age and ethnicity to correlate the risk of colorectal cancer. When the age of the subject is less than 35 years and the base identity at position 351 is homozygous for C or heterozygous, the subject's risk for developing colorectal cancer is assessed to be greater than that of the unaffected relevant population. In one embodiment, the methods are used to assess the risk of colorectal cancer for Hispanic subjects.

Detection of point mutations may be accomplished by molecular cloning of the specified allele and subsequent sequencing of that allele using techniques well known in the art. Alternatively, the gene sequences may be amplified directly from a genomic DNA preparation from the tumor tissue using PCR, and the sequence composition is determined from the amplified product. As described more fully below, numerous methods are available for analyzing a subject's DNA for mutations at a given genetic locus such as the MnSOD gene.

A preferred detection method is allele specific hybridization using probes overlapping the polymorphic site and having about 5, 10, 20, 25, or 30 nucleotides around the polymorphic region. In a preferred embodiment of the invention, several probes capable of hybridizing specifically to the allelic variant are attached to a solid phase support, e.g., a "chip". Oligonucleotides can be bound to a solid support by a variety of processes, including lithography. For example a chip can hold up to 250,000 oligonucleotides (GeneChip, Affymetrix). Mutation detection analysis using these chips comprising oligonucleotides, also termed "DNA probe arrays" is described e.g., in Cronin et al. (1996) Human Mutation 7:244.

In other detection methods, it is necessary to first amplify at least a portion of the MTS of the MnSOD gene prior to identifying the allelic variant. Amplification can be performed, e.g., by PCR and/or LCR, according to methods known in the art. In one embodiment, genomic DNA of a cell is exposed to two PCR primers and amplification for a number of cycles sufficient to produce the required amount of amplified DNA. Preferred primers are listed in Alternative amplification methods include: self sustained sequence replication (Guatelli, J. C. et al., 1990, Proc. Natl. Acad. Sci. USA 87:1874–1878), transcriptional amplification system (Kwoh, D. Y. et al., 1989, Proc. Natl. Acad. Sci. USA 86:1173–1177), Q-Beta Replicase (Lizardi, P. M. et al., 1988, Bio/Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In one embodiment, any of a variety of sequencing reactions known in the art can be used to directly sequence at least a portion of the MTS of the MnSOD gene and detect allelic variants, e.g., mutations, by comparing the sequence of the sample sequence with the corresponding wild-type (control) sequence. Exemplary sequencing reactions include those based on techniques developed by Maxam and Gilbert (Proc. Natl Acad Sci USA (1977) 74:560) or Sanger (Sanger et al (1977) Proc. Nat. Acad. Sci 74:5463). It is also contemplated that any of a variety of automated sequencing procedures may be utilized when performing the subject assays (Biotechniques (1995) 19:448), including sequencing by mass spectrometry (see, for example, U.S. Pat. No. 5,547,835 and international patent application Publication Number WO94/16101, entitled DNA Sequencing by Mass Spectrometryby H. Koster; U.S. Pat. No. 5,547,835 and international patent application Publication Number WO 94/21822 entitled "DNA Sequencing by Mass Spectrometry Via Exonuclease Degradation" by H. Koster), and U.S. Pat. No. 5,605,798 and International Patent Application No. PCT/US96/03651 entitled DNA Diagnostics Based on Mass Spectrometry by H. Koster; Cohen et al. (1996) Adv Chromatogr 36:127–162; and Griffin et al. (1993) Appl Biochem Biotechnol 38:147–159). It will be evident to one skilled in the art that, for certain embodiments, the occurrence of only one, two or three of the nucleic acid bases need be determined in the sequencing reaction. For instance, A-track or the like, e.g., where only one nucleotide is detected, can be carried out.

Yet other sequencing methods are disclosed, e.g., in U.S. Pat. No. 5,580,732 entitled "Method of DNA sequencing employing a mixed DNA-polymer chain probe" and U.S. Pat. No. 5,571,676 entitled "Method for mismatch-directed in vitro DNA sequencing".

In some cases, the presence of the specific allele in DNA from a subject can be shown by restriction enzyme analysis. For example, the specific nucleotide polymorphism can result in a nucleotide sequence comprising a restriction site which is absent from the nucleotide sequence of another allelic variant.

In a further embodiment, protection from cleavage agents (such as a nuclease, hydroxylamine or osmium tetroxide and with piperidine) can be used to detect mismatched bases in RNA/RNA DNA/DNA, or RNA/DNA heteroduplexes (Myers, et al. (1985) Science 230:1242). In general, the technique of "mismatch cleavage" starts by providing heteroduplexes formed by hybridizing a control nucleic acid, which is optionally labeled, e.g., RNA or DNA, comprising a nucleotide sequence of the MnSOD allelic variant with a sample nucleic acid, e.g., RNA or DNA, obtained from a tissue sample. The double-stranded duplexes are treated with an agent which cleaves single-stranded regions of the duplex such as duplexes formed based on basepair mismatches between the control and sample strands. For instance, RNA/DNA duplexes can be treated with RNase and DNA/DNA hybrids treated with S1 nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine whether the control and sample nucleic acids have an identical nucleotide sequence or in which nucleotides they are different. See, for example, Cotton et al (1988) Proc. Natl Acad Sci USA 85:4397; Saleeba et al (1992) Methods Enzymod. 217:286–295. In a preferred embodiment, the control or sample nucleic acid is labeled for detection.

In other embodiments, alterations in electrophoretic mobility is used to identify the MnSOD allelic variant. For example, single strand conformation polymorphism (SSCP) may be used to detect differences in electrophoretic mobility between mutant and wild type nucleic acids (Orita et al. (1989) Proc Natl. Acad. Sci USA 86:2766, see also Cotton (1993) Mutat Res 285:125–144; and Hayashi (1992) Genet Anal Tech Appl 9:73–79). Single-stranded DNA fragments of sample and control nucleic acids are denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In another preferred embodiment, the subject method utilizes heteroduplex analysis to separate double stranded heteroduplex molecules on the basis of changes in electrophoretic mobility (Keen et al. (1991) Trends Genet 7:5).

In yet another embodiment, the identity of the allelic variant is obtained by analyzing the movement of a nucleic acid comprising the polymorphic region in polyacrylamide gels containing a gradient of denaturant, which is assayed using denaturing gradient gel electrophoresis (DGGE) (Myers et al (1985) Nature 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing agent gradient to identify differences in the mobility of control and sample DNA (Rosenbaum and Reissner (1987) Biophys Chem 265:1275).

Examples of techniques for detecting differences of at least one nucleotide between 2 nucleic acids include, but are not limited to, selective oligonucleotide hybridization, selective amplification, or selective primer extension. For example, oligonucleotide probes may be prepared in which the known polymorphic nucleotide is placed centrally (allele-specific probes) and then hybridized to target DNA under conditions which permit hybridization only if a perfect match is found (Saiki et al. (1986) Nature 324:163); Saiki et al (1989) Proc. Natl Acad. Sci USA 86:6230; and Wallace et al. (1979) Nucl. Acids Res. 6:3543). Such allele specific oligonucleotide hybridization techniques may be used for the detection of the nucleotide changes in the polylmorphic region of the MTS of the MnSOD gene. For example, oligonucleotides having the nucleotide sequence of the specific allelic variant are attached to a hybridizing membrane and this membrane is then hybridized with labeled sample nucleic acid. Analysis of the hybridization signal will then reveal the identity of the nucleotides of the sample nucleic acid.

Alternatively, allele specific amplification technology which depends on selective PCR amplification may be used in conjunction with the instant invention. Oligonucleotides used as primers for specific amplification may carry the allelic variant of interest in the center of the molecule (so that amplification depends on differential hybridization) (Gibbs et al (1989) Nucleic Acids Res. 17:2437–2448) or at the extreme 3' end of one primer where, under appropriate conditions, mismatch can prevent, or reduce polymerase extension (Prossner (1993) Tibtech 11:238; Newton et al. (1989) Nucl. Acids Res. 17:2503). This technique is also termed "PROBE" for Probe Oligo Base Extension. In addition it may be desirable to introduce a novel restriction site in the region of the mutation to create cleavage-based detection (Gasparini et al (1992) Mol. Cell Probes 6:1).

In another embodiment, identification of the allelic variant is carried out using an oligonucleotide ligation assay (OLA), as described, e.g., in U.S. Pat. No. 4,998,617 and in Landegren, U. et al., Science 241:1077–1080 (1988). The OLA protocol uses two oligonucleotides which are designed to be capable of hybridizing to abutting sequences of a single strand of a target. One of the oligonucleotides is linked to a separation marker, e.g., biotinylated, and the other is detectably labeled. If the precise complementary sequence is found in a target molecule, the oligonucleotides will hybridize such that their termini abut, and create a ligation substrate. Ligation then permits the labeled oligonucleotide to be recovered using avidin, or another biotin ligand. Nickerson, D. A. et al. have described a nucleic acid detection assay that combines attributes of PCR and OLA (Nickerson, D. A. et al., Proc. Natl. Acad. Sci. (U.S.A.) 87:8923–8927 (1990). In this method, PCR is used to achieve the exponential amplification of target DNA, which is then detected using OLA.

Several techniques based on this OLA method have been developed and can be used to detect the specific allelic variant of the polymorphic region of the MnSOD gene. For example, U.S. Pat. No. 5,593,826 discloses an OLA using an oligonucleotide having 3'-amino group and a 5'-phosphorylated oligonucleotide to form a conjugate having a phosphoramidate linkage. In another variation of OLA described in Tobe et al. ((1996) Nucleic Acids Res 24:3728), OLA combined with PCR permits typing of two alleles in a single microtiter well. By marking each of the allele-specific primers with a unique hapten, i.e. digoxigenin and fluorescein, each OLA reaction can be detected by using hapten specific antibodies that are labeled with different enzyme reporters, alkaline phosphatase or horseradish peroxidase. This system permits the detection of the two alleles using a high throughput format that leads to the production of two different colors.

The invention further provides methods for detecting the single nucleotide polymorphism in the MTS of the MnSOD gene. Because single nucleotide polymorphisms constitute sites of variation flanked by regions of invariant sequence, their analysis requires no more than the determination of the identity of the single nucleotide present at the site of variation and it is unnecessary to determine a complete gene sequence for each patient. Several methods have been developed to facilitate the analysis of such single nucleotide polymorphisms.

In one embodiment, the single base polymorphism can be detected by using a specialized exonuclease-resistant nucleotide, as disclosed, e.g., in Mundy, C. R. (U.S. Pat. No. 4,656,127). According to the method, a primer complementary to the allelic sequence immediately 3' to the polymorphic site is permitted to hybridize to a target molecule obtained from a particular animal or human. If the polymorphic site on the target molecule contains a nucleotide that is complementary to the particular exonuclease-resistant nucleotide derivative present, then that derivative will be incorporated onto the end of the hybridized primer. Such incorporation renders the primer resistant to exonuclease, and thereby permits its detection. Since the identity of the exonuclease-resistant derivative of the sample is known, a finding that the primer has become resistant to exonucleases reveals that the nucleotide present in the polymorphic site of the target molecule was complementary to that of the nucleotide derivative used in the reaction. This method has the advantage that it does not require the determination of large amounts of extraneous sequence data.

In another embodiment of the invention, a solution-based method is used for determining the identity of the nucleotide of the polymorphic site. Cohen, D. et al. (French Patent 2,650,840; PCT Appln. No. WO91/02087). As in the Mundy method of U.S. Pat. No. 4,656,127, a primer is employed that is complementary to allelic sequences immediately 3' to a polymorphic site. The method determines the identity of the nucleotide of that site using labeled dideoxynucleotide derivatives, which, if complementary to the nucleotide of the polymorphic site will become incorporated onto the terminus of the primer.

An alternative method, known as Genetic Bit Analysis or GBA™ is described by Goelet, P. et al. (PCT Appln. No. 92/15712). The method of Goelet, P. et al. uses mixtures of labeled terminators and a primer that is complementary to the sequence 3' to a polymorphic site. The labeled terminator that is incorporated is thus determined by, and complementary to, the nucleotide present in the polymorphic site of the target molecule being evaluated. In contrast to the method of Cohen et al. (French Patent 2,650,840; PCT Appln. No. WO91/02087) the method of Goelet, P. et al. is preferably a heterogeneous phase assay, in which the primer or the target molecule is immobilized to a solid phase.

Recently, several primer-guided nucleotide incorporation procedures for assaying polymorphic sites in DNA have been described (Komher, J. S. et al., Nucl. Acids. Res. 17:7779–7784 (1989); Sokolov, B. P., Nucl. Acids Res. 18:3671 (1990); Syvanen, A.-C., et al., Genomics 8:684–692 (1990); Kuppuswamy, M. N. et al., Proc. Natl. Acad. Sci. (U.S.A.) 88:1143–1147 (1991); Prezant, T. R. et al., Hum. Mutat. 1:159–164 (1992); Ugozzoli, L. et al., GATA 9:107–112 (1992); Nyren, P. et al., Anal. Biochem. 208:171–175 (1993)). These methods differ from GBA™ in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvanen, A.-C., et al., Amer. J. Hum. Genet. 52:46–59 (1993)).

Because the polymorphic region is located in the coding region of the MnSOD gene, yet other methods than those described above can be used for determining the identity of the allelic variant. For example, identification of the allelic variant, which encodes a mutated signal peptide, can be performed by using an antibody specifically recognizing the mutant protein in, e.g., immunohistochemistry or immunoprecipitation. Antibodies to the wild-type or signal peptide mutated forms of the signal peptide proteins can be prepared according to methods known in the art. Preferred antibodies specifically bind to the signal peptide of a human MnSOD having a valine at residue −9. Alternatively, one can also measure an activity of the signal peptide, such as binding to a lipid or lipoprotein. Binding assays are known in the art and involve, e.g., obtaining cells from a subject, and performing binding experiments with a labeled lipid, to determine whether binding to the mutated form of the receptor differs from binding to the wild-type of the receptor.

Antibodies directed against wild type or mutant signal peptides of MnSOD or allelic variants thereof, which are discussed above, may also be used in disease diagnostics and prognostics. Such diagnostic methods, may be used to detect abnormalities in the level of expression of the signal peptide or MnSOD, or abnormalities in the structure and/or tissue, cellular, or subcellular location of the signal peptide or MnSOD. Protein from the tissue or cell type to be analyzed may easily be detected or isolated using techniques which are well known to one of skill in the art, including but not limited to western blot analysis. For a detailed explanation of methods for carrying out Western blot analysis, see Sambrook et al, 1989, supra, at Chapter 18. The protein detection and isolation methods employed herein may also be such as those described in Harlow and Lane, for example, (Harlow, E. and Lane, D., 1988, "Antibodies: A Laboratory Manual", Cold Spring Harbor Laboratory Press, Cold Spring Harbor, N.Y.), which is incorporated herein by reference in its entirety.

This can be accomplished, for example, by immunofluorescence techniques employing a fluorescently labeled antibody (see below) coupled with light microscopic, flow cytometric, or fluorimetric detection. The antibodies (or fragments thereof) useful in the present invention may, additionally, be employed histologically, as in immunofluorescence or immunoelectron microscopy, for in situ detection of MnSOD or its signal peptide or their allelic variants. In situ detection may be accomplished by removing a histological specimen from a patient, and applying thereto a labeled antibody of the present invention. The antibody (or fragment) is preferably applied by overlaying the labeled antibody (or fragment) onto a biological sample. Through the use of such a procedure, it is possible to determine not only the presence of the subject polypeptide, but also its distribution in the examined tissue. Using the present invention, one of ordinary skill will readily perceive that any of a wide variety of histological methods (such as staining procedures) can be modified in order to achieve such in situ detection.

Often a solid phase support or carrier is used as a support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

Moreover, it will be understood that any of the above methods for detecting alterations in a gene or gene product or polymorphic variants can be used to monitor the course of treatment or therapy.

The methods described herein may be performed, for example, by utilizing pre-packaged diagnostic kits, such as those described below, comprising at least one probe or primer nucleic acid described herein, which may be conveniently used, e.g., to determine whether a subject has or is at risk of developing colorectal cancer.

Sample nucleic acid for use in the above-described diagnostic and prognostic methods can be obtained from any cell type or tissue of a subject. For example, a subject's bodily fluid (e.g. blood) can be obtained by known techniques (e.g. venipuncture). Alternatively, nucleic acid tests can be performed on dry samples (e.g. hair or skin). Fetal nucleic acid samples can be obtained from maternal blood as described in International Patent Application No. WO91/07660 to Bianchi. Alternatively, amniocytes or chorionic villi may be obtained for performing prenatal testing.

Diagnostic procedures may also be performed in situ directly upon tissue sections (fixed and/or frozen) of patient tissue obtained from biopsies or resections, such that no nucleic acid purification is necessary. Nucleic acid reagents may be used as probes and/or primers for such in situ procedures (see, for example, Nuovo, G. J., 1992, PCR in situ hybridization: protocols and applications, Raven Press, NY).

In addition to methods which focus primarily on the detection of one nucleic acid sequence, profiles may also be assessed in such detection schemes. Fingerprint profiles may be generated, for example, by utilizing a differential display procedure, Northern analysis and/or RT-PCR.

METHODS OF TREATMENT

The present invention provides for both prophylactic and therapeutic methods of treating a subject having colorectal cancer.

Prophylactic Methods

In one aspect, the invention provides a method for preventing in a subject, colorectal cancer, by administering to the subject an agent which counteracts the unfavorable biological effect of the specific MnSOD allele. Subjects at risk for such a disease can be identified by a diagnostic or prognostic assay, e.g., as described above. Administration of a prophylactic agent can occur prior to the manifestation of symptoms associated with colorectal cancer, such that a disease or disorder is prevented or, alternatively, delayed in its progression. The treatment can also be a specific diet. In particular, the treatment can be undertaken prophylactically, before any other symptoms are present. Such a prophylactic treatment could thus prevent colorectal cancer.

Therapeutic Methods

The invention further provides methods of treating subjects having colorectal cancer. In one embodiment, the method comprises (a) determining the identity of the allelic variant; and (b) administering to the subject a compound that compensates for the effect of the specific allelic variant.

In a preferred embodiment, the identity of the following nucleotide of the MTS of the MnSOD gene of a subject is determined: nucleotide 351.

Generally, the allelic variant can be a mutant allele, i.e., an allele which when present in one, or preferably two copies, in a subject results in a change in the phenotype of the subject. The mutation of the present invention is a substitution of one nucleotide relative to the wild-type allele. The subject can be treated to specifically compensate for the mutation. For example, because the mutation results in an inactive or less active MnSOD, the subject can be treated, e.g., by administration to the subject of a nucleic acid encoding a wild-type MnSOD, such that the expression of the wild-type MnSOD compensates for the endogenous mutated form of the MnSOD. Nucleic acids encoding wild-type human MnSOD protein are comprised of the sequence set forth in SEQ ID No. 1.

Furthermore, based on the site of the mutation in the signal peptide of the MnSOD and the specific effect on its activity, specific treatments can be designed to compensate for that effect as would be obvious to one of ordinary skill in the art.

KITS

As set forth herein, the invention provides methods, e.g., diagnostic and therapeutic methods, e.g., for determining the type of allelic variant of a polymorphic region present in the MnSOD gene, such as a human MnSOD gene. In preferred embodiments, the methods use probes or primers comprising nucleotide sequences which are complementary to the polymorphic region of the MnSOD gene. Accordingly, the invention provides kits for performing these methods.

In a preferred embodiment, the invention provides a kit for determining whether a subject has or is at risk of developing colorectal cancer. The invention also provides kits for determining risk of colorectal cancer containing a first and a second oligonucleotide specific for the polymorphic region of MnSOD. The polymorphic region is found in GenBank Accession No. D83493 shown as SEQ ID NO: 1 in Table 3. Oligonucleotides "specific for" a genetic locus bind either to the polymorphic region of the locus (i.e., the region containing polymorphic residue 351 in the sequence shown in Table 3) or bind adjacent to the polymorphic region of the locus. For oligonucleotides that are to be used as primers for amplification, primers are adjacent if they are sufficiently close to be used to produce a polynucleotide comprising the polymorphic region. In one embodiment, oligonucleotides are adjacent if they bind within about 1–2 kb, and preferably less than 1 kb from the polymorphism. Specific oligonucleotides are capable of hybridizing to a sequence, and under suitable conditions will not bind to a sequence differing by a single nucleotide.

In another embodiment, oligonucleotides are specific for particular alleles including, for example MnSOD Ala allele or the MnSOD Val allele.

In one embodiment the invention provides a kit for determining whether a subject has, or is at risk of developing, colorectal cancer. Such a kit is used to amplify and/or determine the molecular structure of at least a portion of the MnSOD gene and based on that determination one can assess whether the subject has or is at risk of developing colorectal cancer. In a one embodiment, the kit comprises first and second oligonucleotides specific for SEQ ID NO: 1. The first and second oligonucleotides can be used to produce a polynucleotide comprising a region of the MnSOD gene, which includes nucleotide residue 351 of SEQ ID NO: 1. The oligonucleotides preferably have a nucleotide sequence from about 15 to about 30 nucleotides. Preferably, the oligonucleotides are labeled. In one embodiment of the kits of the invention, the first oligonucleotide is specific for the MnSOD Ala allele and the second oligonucleotide is specific for the MnSOD Val allele. Alternatively, the invention provides a kit comprising one or more oligonucleotide probes specific for the MnSOD Ala allele and the MnSOD Val allele. The invention also provides for kits that comprise an allele specific endonuclease.

Preferred kits comprise at least one probe or primer which is capable of specifically hybridizing to the polymorphic region of the MTS of the MnSOD gene and instructions for use. The kits preferably comprise at least one of the above described nucleic acids. Preferred kits for amplifying at least a portion of the MnSOD gene comprise two primers, at least one of which is capable of hybridizing to the MnSOD allelic variant sequence. Such kits are suitable for detection of genotype by, for example, fluorescence detection, by electrochemical detection, or by other detection.

Oligonucleotides, whether used as probes or primers, contained in a kit can be detectably labeled. Labels can be detected either directly, for example for fluorescent labels, or indirectly. Indirect detection can include any detection method known to one of skill in the art, including biotin-avidin interactions, antibody binding and the like. Fluorescently labeled oligonucleotides also can contain a quenching molecule. Oligonucleotides can be boud to a surface. In one embodiment, the preferred surface is silica or glass. In another embodiment, the surface is a metal electrode.

The kits of the invention can also comprise one or more control nucleic acids or reference nucleic acids. For example, a kit can comprise primers for amplifying a polymorphic region of the MTS of the MnSOD gene and a control DNA corresponding to such an amplified DNA and having the nucleotide sequence of a specific allelic variant. Thus, direct comparison can be performed between the DNA amplified from a subject and the DNA having the nucleotide sequence of a specific allelic variant. In one embodiment, the control nucleic acid comprises at least a portion of the MTS of the MnSOD gene of an individual, who does not have colorectal cancer.

Yet other kits of the invention comprise at least one reagent necessary to perform the assay. For example, the kit can comprise an enzyme. Alternatively the kit can comprise a buffer or any other necessary reagent.

Conditions for incubating a nucleic acid probe with a test sample depend on the format employed in the assay, the detection methods used, and the type and nature of the nucleic acid probe used in the assay. One skilled in the art will recognize that any one of the commonly available hybridization, amplification or immunological assay formats can readily be adapted to employ the nucleic acid probes for use in the present invention. Examples of such assays can be found in Chard, T., *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1(1982), Vol. 2 (1983), Vol. 3 (1985); Tijssen, P., *Practice and Theory of Immunoassays: Laboratory Techniques in Biochemistry and Molecular Biology*, Elsevier Science Publishers, Amsterdam, The Netherlands (1985).

The test samples used in the diagnostic kits include cells, protein or membrane extracts of cells, or biological fluids such as sputum, blood, serum, plasma, or urine. The test sample used in the above-described method will vary based on the assay format, nature of the detection method and the tissues, cells or extracts used as the sample to be assayed.

Methods for preparing protein extracts or membrane extracts of cells are well known in the art and can be readily adapted in order to obtain a sample which is compatible with the system utilized.

The kits can include all or some of the positive controls, negative controls, reagents, primers, sequencing markers, probes and antibodies described herein for determining the subject's genotype in the polymorphic region of the MTS of the MnSOD gene.

As amenable, these suggested kit components may be packaged in a manner customary for use by those of skill in the art. For example, these suggested kit components may be provided in solution or as a liquid dispersion or the like.

OTHER USES FOR THE NUCLEIC ACIDS OF THE INVENTION

The identification of the allele of the MnSOD gene can also be useful for identifying an individual among other individuals from the same species. For example, DNA sequences can be used as a fingerprint for detection of different individuals within the same species (Thompson, J. S. and Thompson, eds., Genetics in Medicine, W B Saunders Co., Philadelphia, Pa. (1991)). This is useful, e.g., in forensic studies.

The present invention is further illustrated by the following examples which should not be construed as limiting in any way. The contents of all cited references (including literature references, issued patents, published patent applications as cited throughout this application are hereby expressly incorporated by reference. The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I–IV (D. M. Weir and C. C. Blackwell, eds., 1986); Manipulating the Mouse Embryo, (Cold Spring Harbor Laboratory Press, Cold Spring Harbor, N.Y., 1986).

EXAMPLES

The invention now being generally described, it will be more readily understood by reference to the following examples which are included merely for purposes of illustration of certain aspects and embodiments of the present invention, and are not intended to limit the invention.

The results of the examples here establish that polymorphism associated with the mitochondrial targeting sequence of the MnSOD gene correlates with risk of colorectal cancer. Data from 63 controls and 64 patients with colorectal cancer with known MnSOD genetic polymorphism was obtained. This data demonstrates a significant correlation between polymorphism of the MnSOD gene and susceptibility to colorectal cancer for patient's below a certain age. The data show a significant correlation between cancer risk and the valine-to-alanine exchange in the signal peptide of the MnSOD in association with age of the individual. A T to C substitution in both alleles of the MnSOD gene increases the risk for colorectal cancer in young patients. This shows that cancer risk at younger age may be more highly impacted by oxidative stress, especially by the MnSOD, than in older individuals.

Recent literature shows that MnSOD protein level and activity in normal mucosa vs. tumor are very different from each other. The enzyme levels in many tumors are decreased (3). In colorectal tumors, increased and decreased levels of MnSOD were found (7, 8). Interestingly, the MnSOD activity level increased less than the protein level. It is possible that a change in the secondary structure is responsible for this phenomenon, although it has been shown that reduced activity levels of the MnSOD are not due to a defect in the primary structure of the protein or a decrease in the stability of the mRNA in human tumor cell (9). Further, increased levels of MnSOD in colorectal tumors are associated with poorer 5-year survival and that the MnSOD content of colorectal carcinoma is an independent prognostic marker for overall survival in patients with colorectal cancer (10).

Recognizing the significance of MnSOD in cancer development and the fact that an alteration in the gene sequence predicts an earlier development of the cancer, screening for this genetic alteration may identify young patients at risk for colon cancer. This is the first genetic marker to identify individuals at a high risk for developing.

The examples of the present invention show that the polymorphic region of the MnSOD gene is a significant determinant of an individual's susceptibility to colorectal cancer. Therefore, genotyping patients for the polymorphism of the MTS of the MnSOD gene provides a powerful tool to predict the risk of colorectal cancer.

METHODOLOGY

STUDY POPULATION AND SAMPLE COLLECTION

Incident cases of colorectal cancer in Hispanics and Non-Hispanic White Americans diagnosed at Los Angeles County Hospital and Norris Cancer Center/Univ. of Southern Calif. Los Angeles between 1988 and 1998 were enrolled. The control population consisted of control subjects enrolled in case-control studies of Bladder Cancer and Primary Hepatic Carcinoma at the University of Southern California. Blood samples (10 ml heparinized whole blood) or paraffin tissue was obtained from each subject for extraction of genomic DNA.

GENOTYPIC ANALYSIS OF THE MnSOD GENE

MnSOD alleles were identified using the fluorogenic 5'-nuclease assay (TaqManÒ Assay). The allelic discrimination assay was performed using a TaqManÒ PCR Core Reagent Kit (Applied Biosystems, Foster City, Calif.). The following primers and oligonucleotide probes were used: SEQ ID NO: 3–5'-TGTTTTCTCGTCTTCAGCACC-3' (f), SEQ ID NO:4–5'-GGCTGTGCTTCTGCCTGG-3' (r), SEQ ID NO:5–5'-ATACCCCAAAGCCGGAGCCAG-3' (labeled with 6-FAM) and SEQ ID NO:6–5'-AGATACCCCAAAACCGGAGCCAGC-3' (labeled with CY3, BioSearch Technologies, Novato, Calif.). PCR amplification was performed in a thermal cycler (MWG Biotech, High Point, N.C.): 95° C. for 10 min followed by 2-step cycling of 95° C./25 sec and 63° C./1 min for a total of 37 cycles (blood samples) or 50 cycles (paraffin sample). The fluorescence profile was measured in an ABI 7700 Sequence Detection System and analyzed using Sequence Detection Software (Applied Biosystems). Experimental samples were compared to 8 controls (6 positive, 2 negative) to identify the 3 genotypes at this locus (CC, CT, TT). Any sample that was outside the parameters defined by the controls was identified as non-informative (see FIG. 1).

MnSOD GENOTYPES AND ALLELE FREQUENCIES AMONG HISPANICS WITH COLORECTAL CANCER AND DISEASE FREE CONTROLS

Sixty four (64) Hispanic patients with colorectal cancer and 63 Hispanic disease free controls were screened for this MnSOD polymorphism. Thirty-eight percent (24/64) of cases showed an ALA/ALA genotype, 45% (29/64) an ALA/VAL genotype and 17% (11/64) a VAL/VAL genotype. The frequencies were 0.60 for the alanine allele (ALA) and 0.40 for the valine allele (VAL) respectively. A similar distribution of both alleles was found in the Hispanics control group: ALA/ALA 38% (24/63), ALA/VAL 48% (30/63) and VAL/VAL 14% (9/63), alanine frequency 0.62 and valine frequency 0.38 (Table 1).

MnSOD POLYMORPHISM IN HISPANICS WITH COLORECTAL CANCER: ASSOCIATION WITH AGE

Among Hispanics with colorectal cancer an association between the frequency of the alanine allele and the individual's age was observed. Patients homozygous for the alanine allele (24/64) showed a mean age of 37.6 years compared to 42.3 years for heterozygotes (29/64) and 48.4 years for patients homozygous for the V allele (11/64) (p=0.045, see FIG. 2). The data suggest that the alanine allele of this MnSOD polymorphism might be associated with early age among Hispanics with colorectal cancer. The data in Table 2 show that Hispanics under 35 years of age are more likely to have colorectal cancer when their genotype is Ala/Ala than when their genotype is Val/Val. Thus, it can be concluded that the presence of the alanine allelic variant of MnSOD gene is indicative of a disposition towards colorectal cancer in young patients.

TABLE 1

MnSOD Polymorphism in Hispanics with colorectal cancer and disease free controls

| Genotype | Hispanic controls | Hispanic cases |
|---|---|---|
| ALA/ALA | 24 (38%) | 24 (38%) |
| ALA/VAL | 30 (48%) | 29 (45%) |
| VAL/VAL | 9 (14%) | 11 (17%) |
| TOTAL | 63 (100%) | 64 (100%) |
| ALA-FREQUENCY | 0.62 | 0.60 |
| VAL-FREQUENCY | 0.38 | 0.40 |

*Allele frequencies = $\dfrac{\text{Number of alleles}}{\text{Number of chromosomes}}$

TABLE 2

MnSOD Polymorphism in Hispanics with colorectal cancer

| Genotype | Hispanic cases < 35 years | Hispanic cases ≧ 35 years | p-value |
|---|---|---|---|
| ALA/ALA | 12 (60%) | 14 (32%) | 0.03 |
| ALA/VAL & VAL/VAL | 8 (40%) | 30 (68%) | | p-value is based on Chi-square test

TABLE 3

Partial sequence of human MnSOD from GenBank Accesion No. D83493.
The polymorphic position is position 351. SEQ ID NO:1 is the Val allele
where the residue is C. SEQ ID NO:2 is the Ala allele studied where the
residue is T.

```
ORIGIN
SEQ ID NO:1

1 cggtagcacc agcactagca gcatgttgag ccgggcagtg tgcgggtgag aagaaagggg
 61 acccggtcac ggccccaagg gcgaagggggc tcgcggcggg cagggcctcc gcggcaatgg
121 cgacagtggc cgcaccgggc ctggcgggac cggggcacct gcaggcggtt ctcccggag
181 tgcccggcgc ggcggctgga gcggggatcc gcagggaggg gacgcgggga ctcgggggac
241 gccgcgcgct gccgttcctc ggcagcccag cctgcgtaga cggtccccgc ggcgctgact
301 gaccgggctg tgctttctcg tcttcagcac cagcaggcag ctggctccgg ctttggggta
361 tctgggctcc aggcagaagc acagcctccc cgacctgccc tacgactacg gcgccctg
SEQ ID NO:2

1 cggtagcacc agcactagca gcatgttgag ccgggcagtg tgcgggtgag aagaaagggg
 61 acccggtcac ggccccaagg gcgaagggggc tcgcggcggg cagggcctcc gcggcaatgg
121 cgacagtggc cgcaccgggc ctggcgggac cggggcacct gcaggcggtt ctcccggag
181 tgcccggcgc ggcggctgga gcggggatcc gcagggaggg gacgcgggga ctcgggggac
241 gccgcgcgct gccgttcctc ggcagcccag cctgcgtaga cggtccccgc ggcgctgact
301 gaccgggctg tgctttctcg tcttcagcac cagcaggcag ctggctccgg ttttggggta
361 tctgggctcc aggcagaagc acagcctccc cgacctgccc tacgactacg gcgccctg
```

Those skilled in the art will recognize, or be able to ascertain using no more than routine experimentation, many equivalents to the specific embodiments of the invention described herein. Such equivalents are intended to be encompassed by the following claims.

REFERENCES

1. Oliva, M. R. et al. (1997): Genetic Alterations and Oxidative Metabolism in Sporadic Colorectal Tumors From a Spanish Community. Molecular Carcinogenesis 18:232–243.
2. Ambrosone, C. B. et al. (1999): Manganese Superoxide Dismutase (MnSOD Genetic Polymorphisms, Dietary Antioxidants, and Risk of Breast Cancer. Can. Res. 59, 602–606.
3. Xu, Y. et al. (1999): Mutations in the promotor reveal a cause for the reduced expression of the human manganese superoxide dismutase gene in cancer cells. Oncogene 18(1): 93–102.
4. Shimoda-Matsubayashi, S. et al. (1996): Structural Dimorphism in the Mitochondrial Trageting Sequence in the Human Manganase Superoxide Dismutase Gene. A predictive Evidence for Conformational Change to Influence Mitochondrial Transport and a Study of Allelic Association in Parkinson's Disease. Biochem. Biophys. Res. Commun. 226:561–565.
5. Rosenblum, J. S. et al. (1996): On signal sequence polymorphisms and diseases of distribution. Proc. Natl. Acad. Sci. USA. 93:4471–4473.
6. London, S. J. et al. (1999): Myeloperoxidase Genetic Polymorphism and Lung Cancer Risk. Can. Res. 57:5001–5003.
7. Janssen, A. M. L. et al. (1999): Superoxide dismutase in human colorectal cancer sequence. J Cancer Res. Clin. Oncol. 125:327–335.
8. Van Driel, B. E. M. (1997): Expression of CuZn- and Mn-superoxide dismutase in human colorectal neoplasms. Free Radio. Biol. Med. 23:435–444.
9. St. Clair D. K. and Holland J. C. (1991): Complementary DNA encoding human colon cancer manganese superoxide dismutase and the expression of its gene in human cells. Cancer Res. 51, 939–943.
10. Janssen, A. M. L. et al.(1998): Superoxide dismutases in relation to the overall survival of colorectal cancer patients. Br. J. Cancer 78 (8): 1051–1057.
11. Amstad, P. A. et al. (1997): Manganese superoxide dismutase expression inhibits soft agar growth in JB6 clone41 mouse epidermal cells. Carcinogenesis 18 (3): 479-84.
12. Sun Y. et al. (1988): Superoxide dismutase activity during dimethylhydrazine colon carcinogenesis and the effects of cholic acid and indole. Free Radi. Res. Commun. 4(5): 299–309.
13. Church S. L. et al. (1993): Increased manganese superoxide dismutase expression suppresses the malignant phenotype of human melanoma cells. Proc. Natl. Acad. Sci. USA 90:3113–3117.
14. Iyer, L. and Ratain, M. J. *Eur. J. Cancer* 34:1493-9 (1998).

What is claimed is:

1. A method of determining relative age-related risk of colorectal cancer in a Hispanic subject, comprising:

determining whether a first and/or second allele of a manganese superoxide dismutase (MnSOD) gene in the subject comprise a mutation in the coding region for the mitochondrial targeting sequence (MTS) of the MnSOD protein resulting in a loss of α-helical structure in the MTS;

assigning a lower risk of developing colorectal cancer at an age of less than about 35 years to said subject when the subject has no mutation in either the first or second allele of the MnSOD gene resulting in a loss of α-helical structure in the MTS; and assigning a higher risk of developing colorectal cancer at an age of less than about 35 years to said subject when the subject has mutations in one or both the first and second alleles of the MnSOD gene resulting in a loss of α-helical structure in the MTS;

wherein determining whether said first and/or second allele of the MnSOD gene comprise a mutation in the coding region for the MTS comprises determining whether said first and/or second allele encodes an alanine at position −9 of the MnSOD signal peptide.

2. The method of claim 1 comprising contacting a sample of the subject's nucleic acid comprising the MnSOD gene with a probe or primer which can hybridize to a region of the MnSOD gene encoding the MTS, said region including nucleotide 351 of SEQ ID NO: 1.

3. The method of claim 1, wherein determining whether a first and/or second allele of the MnSOD gene in the subject comprises a mutation in the coding region for the MTS comprises determining the identity of at least one nucleotide of the region encoding the MTS.

4. The method of claim 1, wherein determining whether a first and/or second allele of the MnSOD gene in the subject comprises a mutation in the coding region for the MTS comprises performing a restriction enzyme site analysis.

5. The method of claim 1, wherein determining whether a first and/or second allele of the MnSOD gene in the subject comprises a mutation in the coding region for the MTS comprises performing a single-stranded conformation polymorphism analysis.

6. The method of claim 1, wherein determining whether a first and/or second allele of the MnSOD gene in the subject comprises a mutation in the coding region for the MTS comprises performing an allele specific hybridization.

7. The method of claim 1, wherein determining whether a first and/or second allele of the MnSOD gene in the subject comprises a mutation in the coding region for the MTS comprises performing a primer specific extension.

8. The method of claim 1, wherein determining whether a first and/or second allele of the MnSOD gene in the subject comprises a mutation in the coding region for the MTS comprises performing an oligonucleotide ligation assay.

9. The method of claim 2, wherein the probe or primer has a nucleotide sequence from about 15 to about 30 nucleotides.

10. The method of claim 1, wherein the probe or primer is labeled.

11. The method of claim 1, wherein determining whether said first and/or second allele of the MnSOD gene comprise a mutation in the coding region for the MTS comprises analyzing the genomic DNA of said subject.

12. The method of claim 1; wherein determining whether said first and/or second allele of the MnSOD gene comprise a mutation in the coding region for the MTS comprises sequencing.

13. The method of claim 11; wherein determining whether said first and/or second allele of the MnSOD gene comprise mutation in the coding region for the MTS comprises digesting said genomic DNA with an appropriate restriction endonuclease.

14. The method of claim 1; wherein determining whether said first and/or second allele of the MnSOD gene comprise a mutation in the coding region for the MTS comprises analyzing the RNA of said subject.

15. The method of claim 11; wherein the mutation in the coding region for the MTS resulting in a loss of α-helical structure in the MTS is a C at a position corresponding to position 351 SEQ ID NO: 1.

* * * * *